(12) United States Patent
Watanabe (10) Patent No.: US 11,937,572 B2
(45) Date of Patent: Mar. 26, 2024

(54) AUTOMATICALLY ADJUSTABLE DEVICE FOR AFFIXING TO THE NOSE OF ANIMALS

(71) Applicant: WTA—WATANABE TECNOLOGIA APLICADA LTDA., São Paulo City (BR)

(72) Inventor: Osnir Yoshime Watanabe, São Paulo (BR)

(73) Assignee: WTA—WATANABE TECNOLOGIA APLICADA LTDA., San Paulo State (BR)

( * ) Notice: Subject to any disclaimer, the term of this patent is extended or adjusted under 35 U.S.C. 154(b) by 0 days.

(21) Appl. No.: 16/772,451

(22) PCT Filed: Nov. 29, 2018

(86) PCT No.: PCT/BR2018/050444
§ 371 (c)(1),
(2) Date: Jun. 12, 2020

(87) PCT Pub. No.: WO2019/113661
PCT Pub. Date: Jun. 20, 2019

(65) Prior Publication Data
US 2021/0076639 A1    Mar. 18, 2021

(30) Foreign Application Priority Data
Dec. 14, 2017  (BR) ............ 1020170269418

(51) Int. Cl.
*A01K 15/00*    (2006.01)
*A01K 13/00*    (2006.01)
*A01K 29/00*    (2006.01)

(52) U.S. Cl.
CPC .......... *A01K 15/003* (2013.01); *A01K 13/003* (2013.01); *A01K 29/005* (2013.01)

(58) Field of Classification Search
CPC .. A01K 15/003; A01K 13/003; A01K 29/005; A01K 15/00; A61M 15/00; A61B 5/01; A62B 9/06
(Continued)

(56) References Cited

U.S. PATENT DOCUMENTS 3,788,296 A * 1/1974 Klatt ................ A61D 7/00
                                                    604/93.01
4,369,783 A   1/1983 Hiller et al.
(Continued)

FOREIGN PATENT DOCUMENTS

DE    2125464 A1    12/1972
DE    3045527 A1    7/1982
(Continued)

OTHER PUBLICATIONS

Wo et al., Origin of Long-Term Storage Stability and Nitric Oxide Release Behavior of CarboSil Polymer Doped with S-Nitroso-N-acetyl-d-penicillamine, 2015, ACS Appl Mater Inerfaces (Year: 2015).*
(Continued)

*Primary Examiner* — Joshua J Michener
*Assistant Examiner* — Nicole Paige MacCrate
(74) *Attorney, Agent, or Firm* — B. Aaron Schulman, Esq.; Stites & Harbison, PLLC.

(57) ABSTRACT

The invention relates to an automatically adjustable device for affixing to the nose of animals, which may be used simultaneously for administering medicinal or non-medicinal substances and/or for collecting and transmitting information about the animal by means of onboard sensors, the device being composed of a flexible support body and a pair of adjustable members that are connected by a system of swivel joints, allowing the articulation of the members in all directions. The system of swivel joints enables the adjust-
(Continued)

able members to automatically adjust to the wall of the nasal septum of each animal, which affords greater comfort and offers a larger area of contact between the face of the adjustable members of the device and the nasal mucous membrane of the animal.

12 Claims, 6 Drawing Sheets

(58) Field of Classification Search
USPC .................................. 600/529, 549; 119/866
See application file for complete search history.

(56) References Cited

U.S. PATENT DOCUMENTS

| | | | | |
|---|---|---|---|---|
| 5,533,470 | A * | 7/1996 | Rose | A01K 15/003 |
| | | | | 119/908 |
| 6,701,924 | B1 * | 3/2004 | Land, Jr. | A62B 23/06 |
| | | | | 128/207.18 |
| 2005/0209526 | A1 * | 9/2005 | Ingley, III | A61B 5/6819 |
| | | | | 600/549 |
| 2006/0206120 | A1 * | 9/2006 | Clawson | A61C 19/05 |
| | | | | 606/151 |
| 2016/0235512 | A1 * | 8/2016 | Miller | A61D 7/04 |

FOREIGN PATENT DOCUMENTS

| | | | | |
|---|---|---|---|---|
| EP | 0016431 | A1 * | 10/1980 | ............ A61D 7/00 |
| EP | 0053372 | B1 | 2/1986 | |
| WO | 0064245 | A1 | 11/2000 | |
| WO | 2005/058192 | A2 | 6/2005 | |
| WO | WO-2005058192 | A2 * | 6/2005 | ........... A01K 15/003 |

OTHER PUBLICATIONS

International Search Report and Written Opinion issued in connection with International Application No. PCT/BR2018/050444, dated Feb. 8, 2019.

* cited by examiner

AUTOMATICALLY ADJUSTABLE DEVICE FOR AFFIXING TO THE NOSE OF ANIMALS

The present application claims priority under 35 U.S.C. § 119 to Brazilian Application No. 10 2017 026941 8 filed on Dec. 14, 2017, and under 35 U.S.C. § 365 to International Application No. PCT/BR2018/050444 filed on Nov. 29, 2018. The entire contents of these applications are incorporated herein by reference in their entirety.

The present invention relates to an automatically adjustable device for affixing to the nose of animals, which aim at administering medicinal or non-medicinal substances and/or at collecting and transmitting information about the animal by means of electronic devices, such as electronic sensors.

DESCRIPTION OF THE STATE OF THE ART

Devices for nasal fixation in animals used both for the application of medicinal or non-medicinal substances and for the purpose of monitoring the animal's physical or behavioral conditions are known in the state of the art.

The administration of substances in livestock animals for a prolonged period of time may be necessary for several reasons, among which prophylactic treatment, therapeutic treatment, or even to control the animal's estrous cycle. Currently one of the most used mechanisms is the devices introduced in the reproductive system of the animal, as described in BRPI0802661-0 and WO2016056926.

These devices are usually comprised of a resistant and highly flexible plastic core, so that they have the ability to return to the original shape after manipulation. Additionally, they are covered by a polymer (for example, silicone) impregnated with the substance to be dosed to the animal. They can have different shapes, but allowing an adequate restraint of the device, causing no aggression or irritation to the mucous membrane of the reproductive system.

However, intravaginal devices, as described in said documents, are difficult to apply, since the animal must be immobilized. In addition, due to be internal devices, depending on the distance where an observer is found in the field, it is not possible to verify whether the device is correctly inserted in the animal or, even, if it still remains within the animal.

Thus, the substance administration through a nasal device favors application and control, as it is simpler to introduce into the animal, and for allowing visual control, favoring the identification of which animals received the device, and if the device remains deployed in the animal's nostril.

DE2125464 describes a clamp for the administration of medicinal substances to the nasal mucous membrane of animals, whether they are farmed or domestic animals. According to the technology described, the device has a clamp shape, the members of which carrying the substances are pressed against the nasal mucous membrane wall. Therefore, the members, while fixing the device into the animal's nostril, administrate the desired substance.

In addition, the described device can also be fixed in the nostril through nasal septum perforation, thus presenting an earring shape. The advantages conceived in the scope of this technology would be in the easiness and decrease of the spending time and effort to administrate substances to the animal for a prolonged period of time, in addition to the facility to visualize the device in the animal and the possibility of distinguish by colors.

DE2910629 discloses a device for administering medicated substances to the animal's nasal mucous membrane comprised of a resilient U-shaped (arc) body with inserts at the ends to receive a pair of members carrying the medicinal substances, which will be administered when the members contact the nasal mucous membrane. The device has a specific angulation in the terminal ends of the U-shaped body allowing better anatomical accommodation in the animal's nasal septum and facilitate its introduction into the nostril, thus reducing the impact caused to the animal by the long term use, in addition to the advantages provided by members could be mounted to the body.

DE3045527, on the other hand, describes a device to administrate medicinal substances, whose members carrying the substances are pressed against the nasal mucous membrane wall, and have a triangular shape, with a specific angulation on the face contacting the mucous membrane, increasing the contact area of the device with the nasal mucous membrane.

Furthermore, there are several devices used for the purpose of monitoring the animal, in order to collect information (through sensors such as temperature, moisture, location, movement, heartbeat, respiration and optical) and transmit it (through transponders or transmitters), making it possible to assess the physical and psychological conditions of the animal, and even determine the animal's estrous cycle. Such devices are described in US2015282457 and WO2014201039.

NL1011884 describes a device that can be attached to or inside the nasal septum of animals, preferably cows, for both animal monitoring and substance administration. Said device has measurement means for detecting an animal's physical condition and administering means of active ingredients to the animal. Both measurement and detection means are in direct contact to the animal's nasal mucous membrane. In addition, the measurement means can be associated with several types of sensors, such as temperature sensor, record sensor of heartbeat or breathing rate, among others.

However, the devices for affixing to the nose described herein, although they show constructive changes, whether in the body shape or the contact members, commonly do not fully fulfill the desired function, especially because they do not adequately adjust into the nasal septum of all animals, since each animal has an anatomically different nasal septum, even those of similar breed and size.

By not adjusting perfectly to the animal's nasal septum, these devices may cause some discomfort, and may even generate physical damage to the animal, such as wounds to the nasal septum.

In addition, as they do not adapt correctly to each animal, the contact area between the device and the nasal mucous membrane may be reduced, causing a limitation on the effectiveness of the device, either by not administering the desired substances properly, or not collecting the desired information accurately (for example, temperature and pulse).

Thus, the use of devices for affixing to the nose in animals, with the purpose of administering medicinal substances and/or collecting information about the animal, needing to have a contact area with the nasal mucous membrane arranged in an angle or fixed shape provide only a partial solution for the purposes mentioned above, not fulfilling the objectives satisfactorily and effectively.

Objectives

The objective of at least one embodiment of the present invention is to provide an automatically adjustable device for affixing to the noses of animals that can be used comfortably by animals of different sizes and having greater capacity for collecting and obtaining vital signs from these animals, with greater reliability of the information obtained, said information that will be provided from data and/or notifications via electronic devices.

At least one embodiment of the present invention relates to an automatically adjustable device for affixing to the nose of animals, which aim at administering medicinal or non-medicinal substances and/or at collecting and transmitting information about the animal by means of electronic devices, such as electronic sensors.

Such electronic devices are actively or passively used, optionally, issuing audible and/or luminous warnings, for identification, selection, handling and separation of herds. Such animal information identified by different lights and/or colors presents the situation of the animal and facilitates the identification, selection, manipulation and separation of herds in their respective treatments.

In addition, the automatically adjustable device, as it adapts better to the nasal mucous membrane of the animal, increases the contact area of the nasal mucous membrane with the transmission means comprising the medicinal or non-medicinal substance to be administered to the animal.

BRIEF DESCRIPTION

The objectives of the invention are achieved by an automatically adjustable device for affixing to the nose of animals comprising:
  a pair of adjustable members having a contact surface and a coupling surface; and
  a support body comprising terminal ends with articulated coupling means;
  wherein the coupling surface of each adjustable members is coupled to the articulated coupling means of one of terminal ends of the support body, forming a system of swivel joints; and
  wherein the flat surfaces of the adjustable members are separated by a spacing.

Support body can have at least one of ellipse, circle and rectangle segment shapes and can be made of flexible, elastically deformable material, for example, elastically deformable polymer.

Adjustable members can be at least partially polymeric materials containing at least one treatment substance stored therein. The coupling surface of the adjustable members can be as a female coupling, and the articulated coupling means of the terminal ends can be as a male coupling, for example, the coupling surface of the adjustable members is a spherical concavity, and the articulated coupling means of the terminal ends are sphere-shaped.

The coupling surface of each adjustable members can be coupled to a contact element with a first end attached to the adjustable member and a second opposite end as a male coupling, and the articulated coupling means of the terminal ends can be as a female coupling, for example, the contact element end of the male coupling has a spherical shape, and the articulated coupling means of the terminal ends are as spherical concavity. At least one sensor can be arranged on the adjustable members, with at least one sensor being selected from a temperature sensor and a pulse sensor.

According to an alternative of the invention, the adjustable members comprise a housing consisting of high thermal conductivity material, the housing having a closed end located on the face of the adjustable members facing the nasal septum mucous membrane of the animal, and the temperature sensor is arranged in the housing.

At least one of an electronic transmitter, a motion sensor, an optical electronic sensor, a location sensor, a respiration sensor, and a moisture sensor can be arranged in the support body.

BRIEF DESCRIPTION OF THE DRAWINGS

The present invention will now be described in more detail based on an exemplary embodiment shown in the drawings. The figures show.

DETAILED DESCRIPTION OF THE FIGURES

FIGS. 1 to 8 show a first embodiment of the automatically adjustable device for affixing to the nose 20 of animals. The device 20 comprises a pair of adjustable members 1 and a support body 2 made of a flexible, elastically deformable material, such as a polymer, allowing the adjustment of the distance between the adjustable members, and facilitating the comfortable fitting of the device 20 in the animal's nostril, regardless of the width of the nostril. The deformation elastic resistance of the flexible material causes the support body 2 to exert slight pressure on the front face of the adjustable members 1.

Support body 2 also has an ellipse segment shape. In a possible constructive variation, the support body 2 may take a circle or rectangle segment shape.

Figure 1:
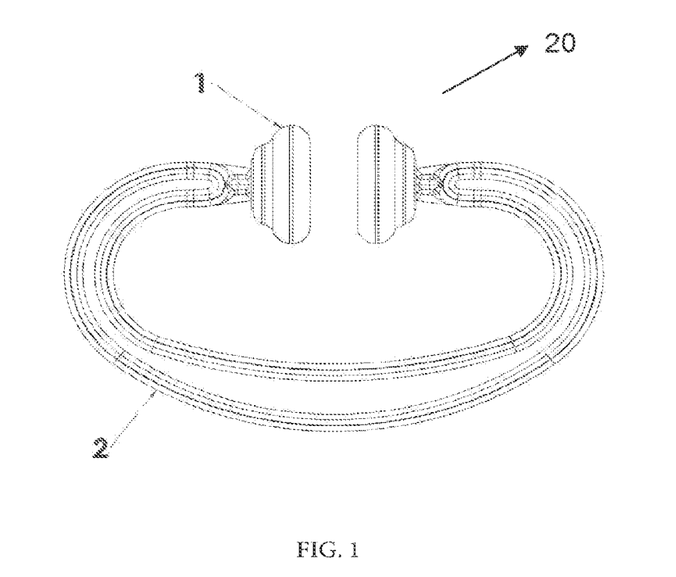
FIG. 1 is a front view of the first embodiment of the device.
Figure 2:
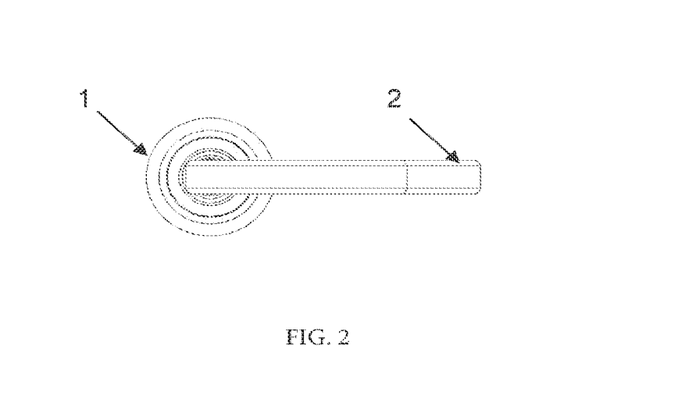
FIG. 2 is a lateral view of the first embodiment of the device.
Figure 3:
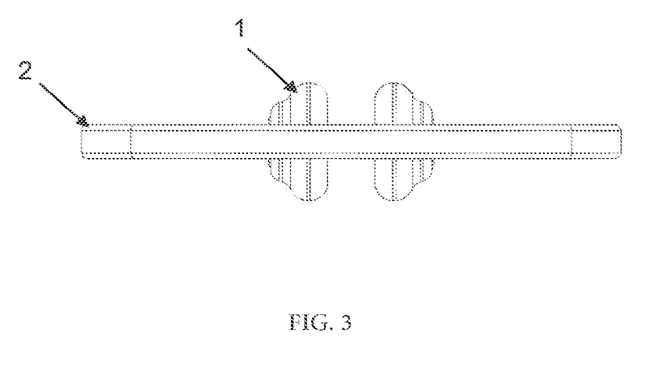
FIG. 3 is a bottom view of the first embodiment of the device.
Figure 4:
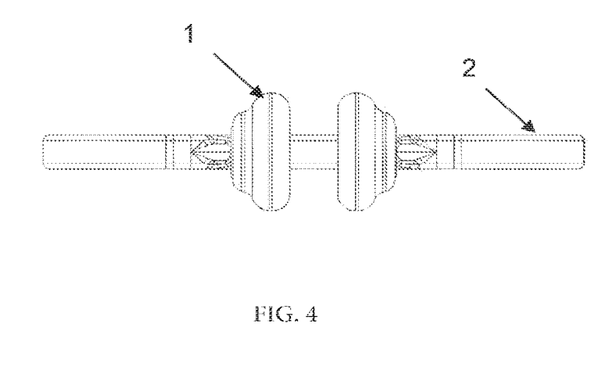
FIG. 4 is a top view of the first embodiment of the device.
Figure 5:
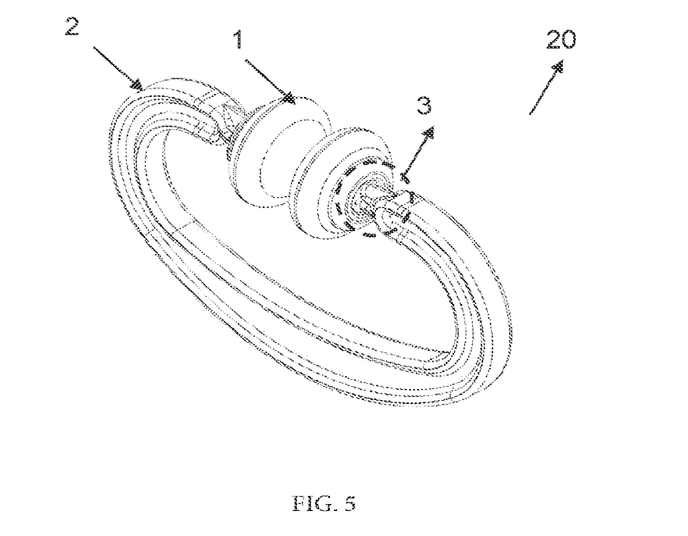
FIG. 5 is a perspective view of the first embodiment of the device.
Figure 6:
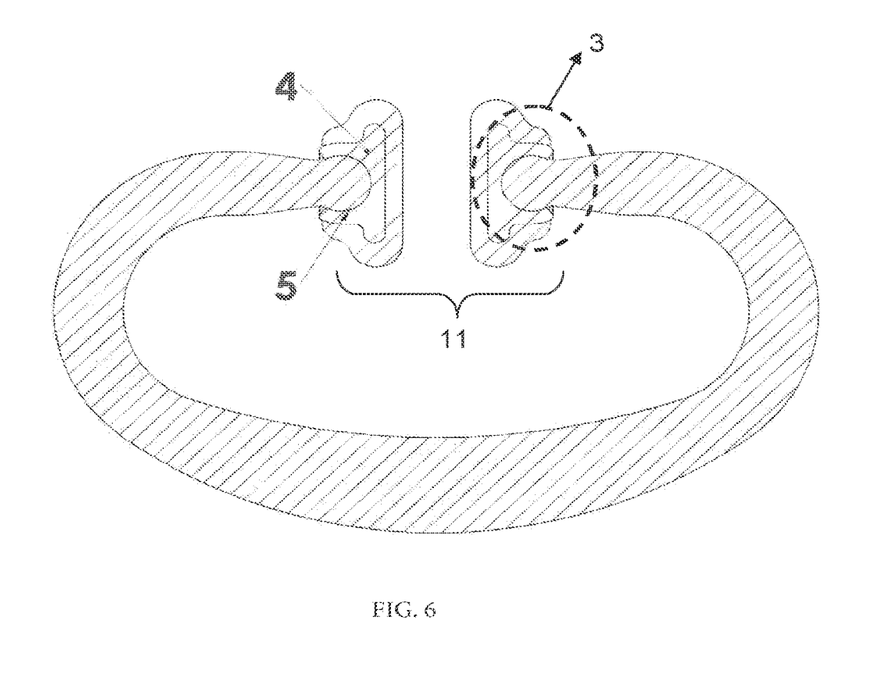
FIG. 6 is a cross-section view of the first embodiment of the device.
Figures 7, 8:
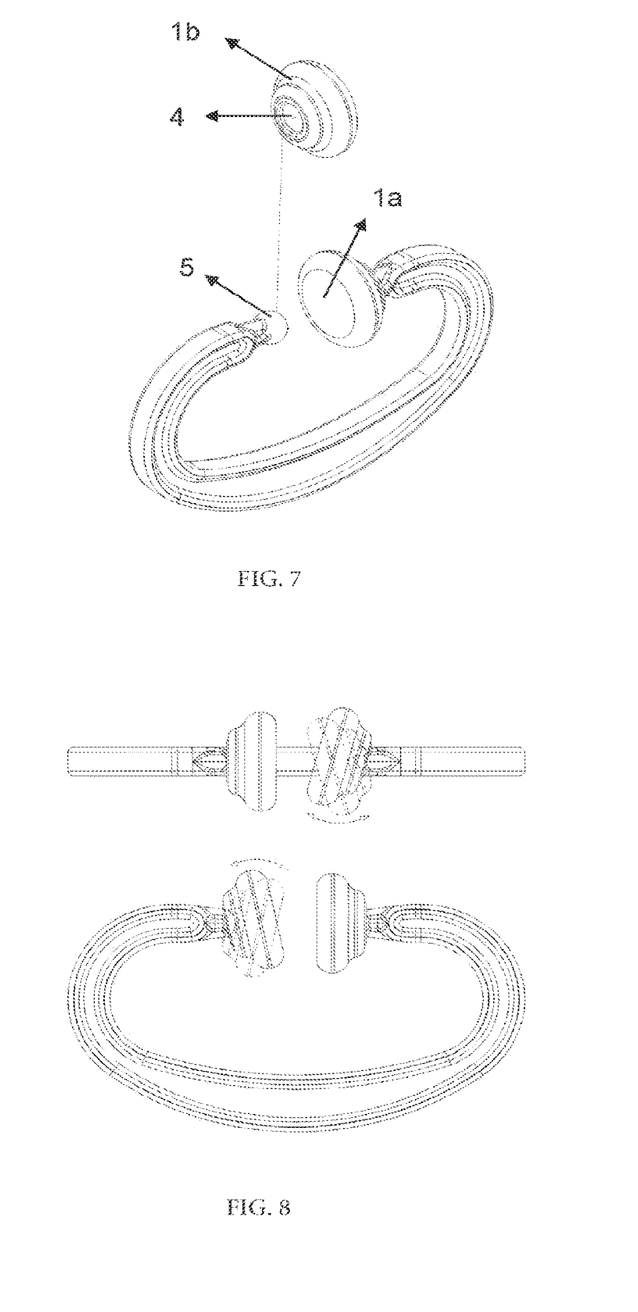
FIG. 7 is an expanded view of the first embodiment of the device.
FIG. 8 is the swivel joint representation of the members of the first embodiment of the device.

Each of the adjustable members 1 are attached to one end of the support body 2. These adjustable members 1 each have a contact surface 1a and a coupling surface 1b for articulated coupling, with freedom of rotation, with the terminal end 5 of the support body 2. According to this first embodiment of the invention, the coupling surface 1b has a concavity 4 as a female coupling, preferably spherical, with an opening, as shown in FIG. 7.

Concavity 4 of each adjustable members 1 will be attached to a terminal end 5 provided with articulated coupling means of the support body 2. According to the first embodiment of the invention shown in FIGS. 1 to 8, each terminal ends 5 has male coupling means, preferably spherical and with a size compatible with that of the concavity 4, so that it will be connected to that respective concavity 4. Thus, the flat surfaces 1a will be facing each other and separated by a spacing 11.

The connection between the concavities 4 of the adjustable members 1 and the terminal ends 5 of the support body 2 will form a system of swivel joints 3, which will allow the articulation of the adjustable members 1 in all directions. This articulation of movements allows a better adjust of the device into the animal's nasal septum on both sides.

Additionally, the adjustable members 1 are at least partially made up of polymeric materials containing at least one medicinal substance (animal treatment substances) stored therein, the substance of which is to be administered to the animal. It can be entirely made up of this material containing said substance, or just coated with it.

Thus, in this first embodiment, the system of swivel joints 3 will also allow the entire contact surface 1a of the adjustable members 1 to be in constant contact to the animal's nasal mucous membrane regardless of the anatomical shape, increasing the contact area of the device 20 with the animal's nasal mucous membrane as a whole.

Therefore, this shape for device 20 is ideal for the administration of treatment substances, since the contact of members 1 to the mucous membrane will be constant and greater, allowing the release of the appropriate amount of treatment substance to be administered, with no waste.

Figure 9:
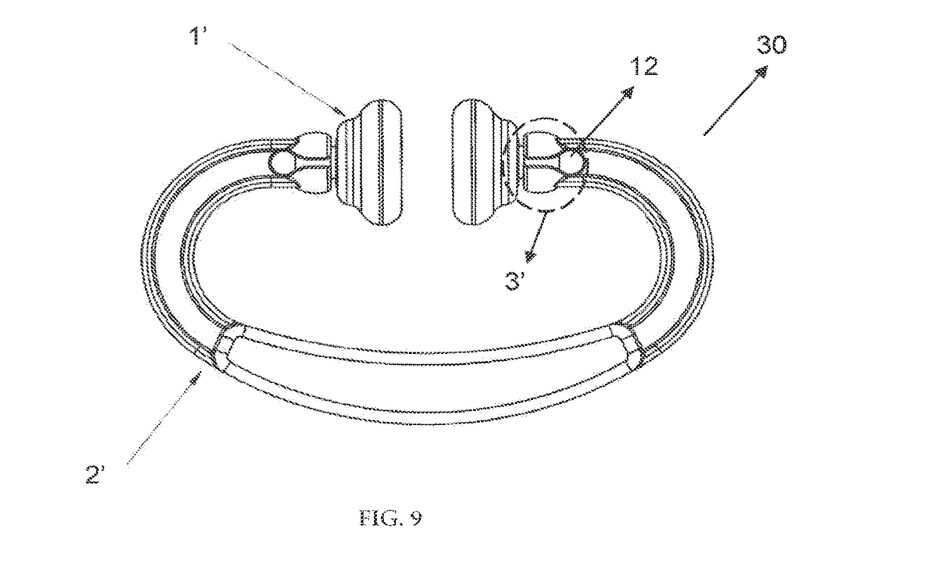
FIG. 9 is a front view of the second embodiment of the device.
Figure 10:
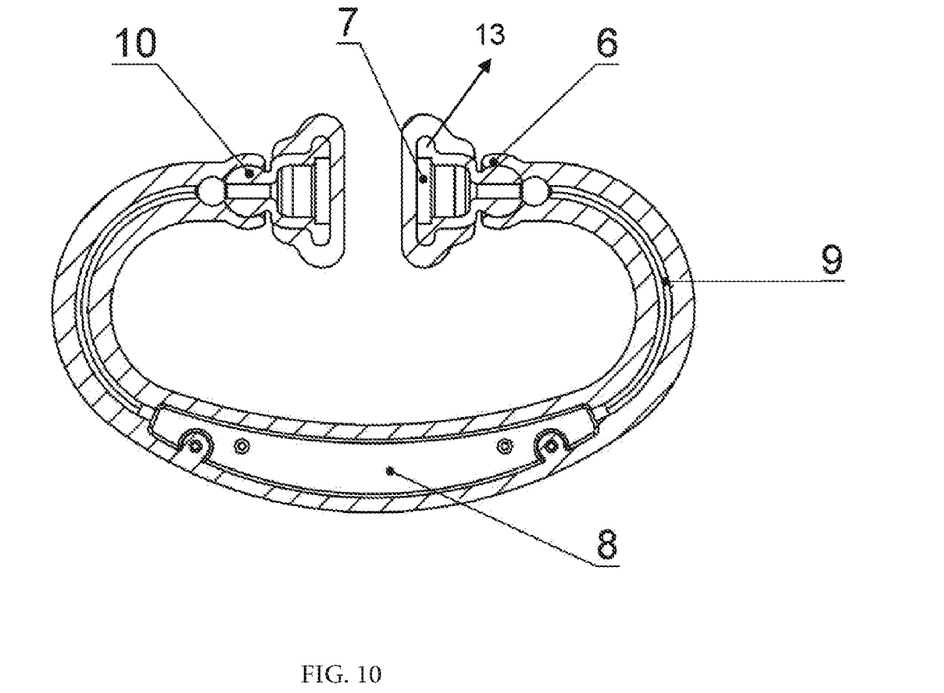
FIG. 10 is a cross-section view of the second embodiment of the device.
Figure 11:
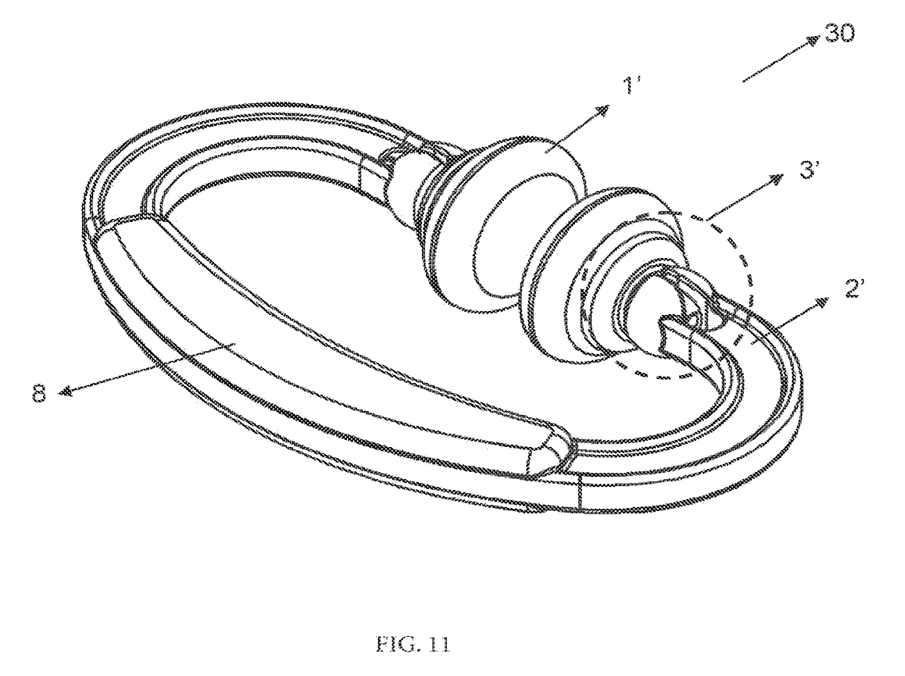
FIG. 11 is a perspective view of the second embodiment of the device.

FIGS. 9 to 11 show a second embodiment of an automatically adjustable device for affixing to the nose 30, which is preferably used when there is a need to collect information of the animal.

In this embodiment, the support body 2' has terminal ends 6 with coupling means configured as a female coupling, preferably as a spherical concavity. The pair of adjustable members 1' has a contact element 12 with an end attached to the adjustable member 1' and the terminal opposite end configured as a male coupling having a shape compatible with the female coupling of the terminal ends 6 of the support body 2', preferably a spherical shape 10.

Thus, the terminal end 10 of the contact element 12 will be connected to one terminal ends 6 of the support body 2', also forming a system of swivel joints 3'.

In this second embodiment, the shape of the adjustable members 1' with its protruding rear face 10 forming a male coupling increases the space available inside the adjustable member 1', which facilitates the assignment of electronic devices, particularly electronic sensors 7, such as, for example, temperature and pulse sensors. However, such sensors can also be integrated with the adjustable means 1, according to the first embodiment of the invention.

In any of the embodiments of the invention, an electronic transmitter and a battery (not shown) of sensor 7 can be installed in the lower region 8 of the support body 2, so that the communication between the sensors 7 and the transmitter can be performed through a channel 9.

In addition, such electronic devices, for example, sensors (not shown) which does not need to be in direct contact with the animal (such as movement, optical, location and moisture sensor) can also be installed in the lower region 8 support body 2. Such sensors may also contain a sound-emitter (not shown) and a light-emitter (not shown) in which they can also be fixed to be exposed to the support body 2 in order to notify information collected by the device or to transmit identifications.

The adjustable members 1' can also comprise a housing 13 preferably made of metallic material or another high thermal conductivity material receiving a temperature sensor 7 within. The closed end of the housing 13 is located on the front face of the adjustable members 1', so as to be in direct contact with the nasal septum mucous membrane of the animal, which improves the accuracy in temperature reading, and minimizes the interference caused by the air flow caused by the breath of the animal or the wind.

Therefore, due to the system of swivel joints 3' associated with the male coupling in the terminal members 1', this second embodiment of the invention allows the adjustable members 1' provided with sensors to always be in contact with the nasal septum mucous membrane of the animal, improving the data quality and accuracy measured, contributing to a better health analysis of the animal.

The association between the support body 2, 2' made of flexible and resistant material and the system of swivel joints formed by the coupling of the adjustable members 1, 1' with the support body 2, 2' allows the pressure exerted by the support body 2, 2' on the adjustable members 1, 1' is transmitted against the nasal mucous membrane of the animal, thus serving to adjust the adjustable members 1, 1' at the angle that best suits the anatomy of nasal septum of the animal, and also to fix the device 20, 30 in the animal's nostril.

Thus, the automatically adjustable device for affixing to the nose 20, 30 as conceived in both embodiments, offers the following advantages over previously known counterparts:
  greater contact area between device 20, 30 and the nasal mucous membrane of the animal, favoring the administration of treatment substances, and/or also the accuracy in collecting information about animals, through electronic devices, for instance, sensors;
  greater comfort to the animal, and less incidence of physical damage caused by the long-term use provided by the system of swivel joints which allows the best adjustment of the device to the anatomy of each animal;
  greater spatial capacity for sensors to be physically integrated into the device, maintaining the accuracy degree of the readings made by these sensors.

The examples of preferred embodiments have been described, it should be understood the scope of the present invention encompasses other possible variations, being limited just by the content of the claims only, including possible equivalents therein.

The invention claimed is:

1. An automatically adjustable device for affixing to the nose of animals, said device comprising:
  a pair of adjustable members having flat surfaces and a coupling surface; and
  a support body separate from the adjustable members comprising terminal ends forming articulated coupling means, wherein the coupling surface of each of the adjustable members is coupled to a respective articulated coupling means of the terminal ends of the support body, forming a system of swivel joints; and
  wherein the flat surfaces of the adjustable members are separated by a spacing;
  wherein the adjustable members are at least partially polymeric materials containing at least one treatment substance stored therein;
  wherein the coupling surface of the adjustable members is a female coupling, and the articulated coupling means of the terminal ends are a male coupling;
  wherein the coupling surface of the adjustable members is a spherical concavity, and the articulated coupling means of the terminal ends has a spherical shape and
  wherein at least one electronic device is positioned in a space formed in the adjustable members.

2. An automatically adjustable device for affixing to the nose according to claim 1, wherein the support body is made of flexible, elastically deformable material.

3. An automatically adjustable device for affixing to the nose according to claim 2, wherein the support body is made of elastically deformable polymer.

4. An automatically adjustable device for affixing to the nose of animals according to claim 1, wherein the electronic device is a sensor selected from a temperature sensor and a pulse sensor.

5. An automatically adjustable device for affixing to the nose of animals according to claim 4, wherein the sensor is a temperature sensor that is housed at the housing.

6. An automatically adjustable device for affixing to the nose of animals according to claim 1, wherein the adjustable members comprise a housing consisting of high thermal conductivity material.

7. An automatically adjustable device for affixing to the nose of animals according to claim 6, wherein the housing has a closed end located on the face of the adjustable members facing the nasal septum mucous membrane of the animal.

8. An automatically adjustable device for affixing to the nose of animals according to claim 1, wherein the electronic device is least one of an electronic transmitter, a motion sensor, an optical electronic sensor, a location sensor, a respiration sensor and a moisture sensor arranged on the support body.

9. An automatically adjustable device for affixing to the nose of animals according to claim 8, wherein the electronic device is a transmitter that comprises a sound-emitter and/or light-emitter.

10. An automatically adjustable device for affixing to the nose according to claim 1, wherein the support body has at least one shape selected from the group consisting of an ellipse, circle, and a rectangle segment.

11. An automatically adjustable device for affixing to the nose of animals, said device comprising:
 a pair of adjustable members which have flat surfaces and a coupling surface; and
 a support body separate from the adjustable members comprising terminal ends forming articulated coupling means, wherein the coupling surface of each of the adjustable members is coupled to a respective articulated coupling means of the terminal ends of the support body, forming a system of swivel joints; and
 wherein the flat surfaces of the adjustable members are separated by a spacing;
 wherein the adjustable members are at least partially polymeric materials containing at least one treatment substance stored therein;
 wherein the coupling surface of each adjustable members is coupled to a contact element with a first end attached to the adjustable member and a second opposite end being a male coupling, and the articulated coupling means of the terminal ends are a female coupling;
 wherein the end of the contact element is a male coupling having a spherical shape, and the articulated coupling means of the terminal ends are spherical cavities; and
 wherein at least one electronic device is positioned in a space formed in the adjustable members.

12. An automatically adjustable device for affixing to the nose of animals, said device comprising a pair of adjustable members which have flat surfaces and a coupling surface; and a support body comprising terminal ends with articulated coupling means,
 wherein the coupling surface comprises a spherical concavity, and said articulated coupling means of the terminal ends are sphere-shaped
 wherein the coupling surface is coupled to the articulated coupling means of the terminal ends in said support body, forming a system of swivel joints, the system of swivel joints allowing the articulation of the adjustable members in all directions;
 wherein the coupling surface of each of the adjustable members is coupled to a contact element with a first end attached to the adjustable member and a second opposite end being a male coupling, and the articulated coupling means of the terminal ends being a female coupling;
 wherein the end of the contact element of the male coupling has a spherical shape, and the articulated coupling means of the terminal ends form a spherical concavity;
 wherein the flat surfaces of the adjustable members are separated by a spacing;
 wherein the adjustable members are at least partially polymeric materials containing at least one treatment substance stored therein; and at least one means of electronic devices arranged on the adjustable members, wherein said electronic devices comprise at least one sensor.

* * * * *